United States Patent
Tae et al.

(10) Patent No.: US 10,973,933 B2
(45) Date of Patent: Apr. 13, 2021

(54) NANOPARTICLES FOR DIAGNOSIS AND TREATMENT OF TUMORS

(71) Applicant: GWANGJU INSTITUTE OF SCIENCE AND TECHNOLOGY, Gwangju (KR)

(72) Inventors: Giyoong Tae, Gwangju (KR); Abhishek Sahu, Gwangju (KR); Jong Hyun Lee, Gwangju (KR)

(73) Assignee: GWANGJU INSTITUTE OE SCIENCE AND TECHNOLOGY, Gwangju (KR)

( * ) Notice: Subject to any disclaimer, the term of this patent is extended or adjusted under 35 U.S.C. 154(b) by 202 days.

(21) Appl. No.: 15/291,071

(22) Filed: Oct. 12, 2016

(65) Prior Publication Data

US 2017/0106102 A1 Apr. 20, 2017

(30) Foreign Application Priority Data

Oct. 14, 2015 (KR) .......................... 10-2015-0143475

(51) Int. Cl.
  *A61K 49/00* (2006.01)
  *A61K 41/00* (2020.01)

(52) U.S. Cl.
  CPC ...... *A61K 49/0093* (2013.01); *A61K 41/0052* (2013.01); *A61K 41/0057* (2013.01); *A61K 49/003* (2013.01); *A61K 49/0034* (2013.01)

(58) Field of Classification Search
  None
  See application file for complete search history.

(56) References Cited

U.S. PATENT DOCUMENTS

2014/0271487 A1* 9/2014 Fernandes .............. A61K 9/143
  424/9.6
2015/0065858 A1* 3/2015 Chen .................... A61K 49/183
  600/411

OTHER PUBLICATIONS

Sheng, Z., et al., "Smart Human Serum AlbuminIndocyanine Green Nanoparticles Generated by Programmed Assembly for Dual-Modal Imaging-Guided Cancer Synergistic Phototherapy", ACS NANO, 2014, pp. 12310-12322.*
Hong, C., et al., "Amperometric Immunosensor for the Determination of a-1-Fetoprotein Based on Core-Shell-Shell Prussian Blue-BSA-Nanogold Functionalized Interface", Electroanalysis, 2008, pp. 2185-2191.*
Ishizawa, T., et al., "Real-Time Identification of Liver Cancers by Using Indocyanine Green Fluorescent Imaging", Cancer, 2009, pp. 2491-2504.*
Master, A., et al., "Photodynamic Nanomedicine in the Treatment of Solid Tumors: Perspectives and Challenges", J. Control. Release, 2013, pp. 88-102.*
Oh, Y., et al., "Intraoperative combined color and fluorescent images-based sentinelnode mapping in the porcine lung: Comparison of indocyanine greenwith or without albumin premixing", J. Thoracic Card. Surg., pp. 1509-1515 (Year: 2013).*
Mordon, S., et al., "Indocyanine Green: Physicochemical FactorsAffecting Its Fluorescencein Vivo", Microvascular Res., pp. 146-152 (Year: 1998).*
Awasthi, K., et al., "Modification of near-infrared cyanine dyes by serum albumin proteins", Photchem. Photobio. Sci., pp. 461-463 (Year: 2011).*
Liang Cheng et al., "PEGylated Prussian blue nanocubes as a theranostic agent for simultaneous cancer imaging and photothermal therapy", Biomaterials 35, 2014, pp. 9844-9852.
Matthieu F. Dumont et al., "Biofunctionalized Gadolinium-Containing Prussian Blue Nanoparticles as Multimodal Molecular Imaging Agents", Bioconjugate Chemistry 25, 2014, American Chemical Society Publications, pp. 129-137.

* cited by examiner

Primary Examiner — Michael G. Hartley
Assistant Examiner — Lance W Rider
(74) Attorney, Agent, or Firm — Hauptman Ham, LLP

(57) ABSTRACT

Disclosed herein are nanoparticles for diagnosis or treatment of tumors. The nanoparticles include: (a) a core including a Prussian blue dye; and (b) a shell obtained by partially or completely coating a surface of the Prussian blue core with albumin, thereby diagnosing a tumor by a nuclear magnetic resonance imaging apparatus and a near-infrared fluorescence imaging apparatus and necrotizing a tumor by a combined photothermal-photodynamic effect.

6 Claims, 18 Drawing Sheets

Total removal of tumors

NANOPARTICLES FOR DIAGNOSIS AND TREATMENT OF TUMORS

CROSS REFERENCE TO RELATED APPLICATION

This application claims the priority of Korean Patent Application No. 10-2015-0143475, filed on Oct. 14, 2015 in the KIPO (Korean Intellectual Property Office), the disclosure of which is incorporated herein by reference in its entirety.

BACKGROUND

1. Technical Field

The present invention relates to nanoparticles for diagnosis or treatment of tumors, which can diagnose a tumor through a nuclear magnetic resonance imaging apparatus and a near-infrared fluorescence imaging apparatus and can necrotize the tumor through a combined photothermal-photodynamic effect.

2. Description of the Related Art

In the field of biotechnology, nanoparticles are used for tumor tissue-specific killing, boosting of immune responses, cell fusion, gene or drug delivery, diagnosis, and the like. To be used for these purposes, nanoparticles need to have a portion to which an active component can be attached and need to be easily transported and dispersed in a living body, that is, in an aqueous environment.

Recently, theranostic nanoparticles which can be simultaneously used for diagnosis and treatment are attracting attention as a promising nanomaterial for treating cancer. If various capabilities for diagnosis and treatment can be realized in a single material, it can be very useful for clinical applications.

However, since there are almost no materials capable of diagnosing and treating tumor tissue, various types of functional materials having the features set forth above are being developed. Specifically, since high sensitivity of near-infrared fluorescence imaging and high spatial resolution of nuclear magnetic resonance imaging complement each other, and combination of photodynamic therapy (PDT) and photothermal therapy (PTT) can provide a better treatment system than anything else, a nanomaterial satisfying all of the functionalities set forth above is required.

Prussian blue (PB) can serve as an MRI contrast agent as PB and analogues have magnetic properties. In addition, PB nanoparticles are recently rising as a new generation of a photothermal agent due to high absorption in the NIR spectrum. Thus, several theranostic nanoparticles have been developed using PB nanoparticles in recent years.

In recent studies of a nanoparticle synthesis system using PB, citric acid stabilization is mainly used. However, nanoparticles obtained using citric acid stabilization are not suitable for in vivo application, particularly, through intravenous infusion.

Moreover, in the past, surface coating with a polymer including PEG and PVA was used for surface stabilization of nanoparticles including PB. The suitability of these nanoparticles for in vivo application through intravenous infusion is unknown.

Therefore, there is a need for nanoparticles including materials approved for use in humans to enable in vivo injection and including PB to enable diagnosis of a position of tumor tissue and treatment of the tumor tissue by necrosis.

BRIEF SUMMARY

It is an aspect of the present invention to provide nanoparticles for diagnosis or treatment of tumors, which can diagnose a tumor through a nuclear magnetic resonance imaging apparatus and a near-infrared fluorescence imaging apparatus and can necrotize the tumor through a combined photothermal-photodynamic effect.

It is another aspect of the present invention to provide a method of diagnosing or treating an in vivo tumor of mammals except humans using the nanoparticles as set forth above.

In accordance with one aspect of the present invention, nanoparticles for diagnosis or treatment of tumors are Prussian blue-albumin nanoparticles including: (a) a core including a Prussian blue dye; and (b) a shell obtained by partially or completely coating a surface of the Prussian blue core with serum albumin.

The nanoparticles for diagnosis or treatment of tumors may be Prussian blue-albumin-fluorescent dye nanoparticles obtained by impregnating the albumin of the shell with a near-infrared fluorescent dye.

The near-infrared fluorescent dye may include at least one selected from the group consisting of indocyanine green (ICG), Cy3.5, Cy5, Cy5.5, Cy7, cypate, and methylene blue (MB).

The Prussian blue may be mixed with the albumin in a molar ratio of 10:1 to 100:1.

The near-infrared fluorescent dye may be present in an amount of up to 60% by weight (wt %) in the nanoparticles for diagnosis or treatment of tumors.

The Prussian blue-albumin nanoparticles may increase a temperature of an in vivo tumor of mammals except humans to 45° C. or more, preferably 45° C. to 90° C., when irradiated with a near-infrared laser beam.

Although the Prussian blue-albumin-fluorescent dye nanoparticles are nontoxic in the absence of light, the Prussian blue-albumin-fluorescent dye nanoparticles can increase the temperature of an in vivo tumor of mammals except humans to 45° C. or more, preferably 55° C. to 90° C., and generate reactive oxygen species when irradiated with a near-infrared laser beam.

The Prussian blue-albumin-fluorescent dye nanoparticles may include at least one selected from the group consisting of photodynamic therapeutic drugs of porphyrin, methylene blue or phthalocyanine; and anticancer agents of paclitaxel, doxorubicin, curcumin or docetaxel.

The nanoparticles may exhibit a fluorescence signal at a tumor site that is 2 or more times, preferably 2 times to 5 times, that at a non-tumor site.

In accordance with another aspect of the present invention, a method of diagnosing or treating an in vivo tumor of mammals except humans includes: (A) injecting the nanoparticles as set forth above into a living body or specimen of mammals except humans; and (B) diagnosing the presence or absence of a tumor and a position of the tumor by sensing a signal emitted from the injected nanoparticles.

In operation (B), the signal may be sensed by a nuclear magnetic resonance imaging apparatus and a near-infrared fluorescence imaging apparatus.

In operation (B), the signal may be sensed 5 hours to 25 hours after injection of the nanoparticles.

The method may further include selectively necrotizing only a tumor cell by irradiating the tumor cell with a near-infrared laser beam, after injection of the nanoparticles. The near-infrared laser beam may be irradiated 5 hours to 25 hours after injection of the nanoparticles.

According to the present invention, since the nanoparticles for diagnosis or treatment of tumors are accumulated only in tumor tissue and are not accumulated in non-tumor tissue, the nanoparticles can diagnose the presence or absence of tumor tissue and a position of tumor tissue by a nuclear magnetic resonance imaging apparatus and a near-infrared fluorescence imaging apparatus. In addition, when the nanoparticles according to the present invention are irradiated with a near-infrared laser beam after injection of the nanoparticles, the nanoparticles can necrotize all tumor tissue by a combined photothermal-photodynamic effect, and tumor tissue does not grow again after laser irradiation. The reason of this is that, although the nanoparticles for diagnosis or treatment of tumors according to the present invention are nontoxic in the absence of light, the nanoparticles exhibit toxicity and thus necrotize all tumor tissue by the combined photothermal-photodynamic effect when irradiated with a near-infrared laser beam.

In addition, the nanoparticles for diagnosis or treatment of tumors according to the present invention include only biocompatible materials, and any organic solvents or chemical crosslinking agents are not used in the preparation of the nanoparticles.

BRIEF DESCRIPTION OF THE DRAWINGS

The above and other aspects, features, and advantages of the present invention will become apparent from the detailed description of the following embodiments in conjunction with the accompanying drawings.

DETAILED DESCRIPTION

Figure 1A:
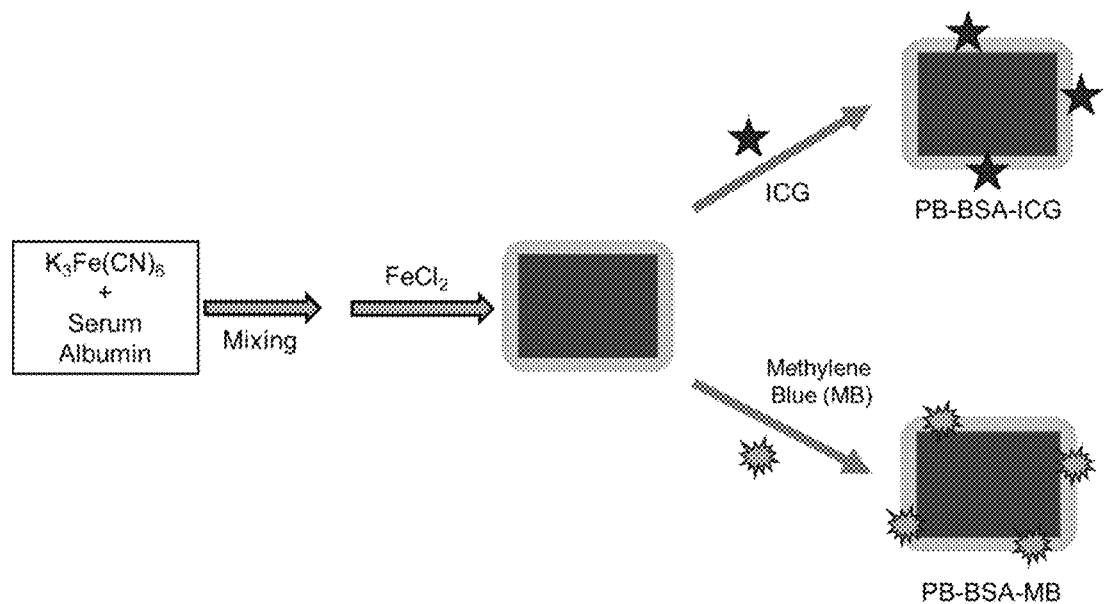
FIG. 1a shows schematic diagrams of PB-BSA nanoparticles produced in Example 1 and PB-BSA-ICG or PB-BSA-MB nanoparticles produced in Example 2.

The present invention relates to nanoparticles for diagnosis or treatment of tumors, which can diagnose a tumor through a nuclear magnetic resonance imaging apparatus and a near-infrared fluorescence imaging apparatus and can necrotize the tumor through a combined photothermal-photodynamic effect.

The nanoparticles according to the present invention are produced using clinically approved biocompatible materials, exhibit excellent stability in an aqueous physiological solution, and effectively increase stability of a near-infrared fluorescent dye (for example, indocyanine green) included therein with respect to light The nanoparticles according to the present invention may be used for combined photothermal/photodynamic treatment as well as for dual mode nuclear magnetic resonance (MR) imaging and near-infrared (NIR) fluorescence imaging. In addition, although the nanoparticles according to the present invention are nontoxic in the absence of light, the nanoparticles allow significant necrosis of cells by a photothermal-photodynamic effect when irradiated with a near-infrared laser beam. Further, when intravenously injected into a mouse having a tumor, the nanoparticles according to the present invention are mainly accumulated in the tumor while minimizing non-specific accumulation thereof in major organs. This may be confirmed by nuclear magnetic resonance imaging and near-infrared fluorescence imaging. Finally, tumor tissue of a mouse, into which the nanoparticles according to the present invention are injected, is effectively removed after irradiation with a near-infrared laser beam, and does not regrow.

Hereinafter, embodiments of the present invention will be described in detail.

According to the present invention, core-shell nanoparticles for diagnosis or treatment of tumors include: (a) a core including a Prussian blue dye; and (b) a shell obtained by partially or completely coating a surface of the Prussian blue core with albumin. In addition, the albumin of the shell may be impregnated with a near-infrared fluorescent dye.

The Prussian blue (PB) dye included in the core is iron (III) hexacyanoferrate mixed with $Fe_4[Fe(CN)_6]_3 \cdot xH_2O$, and is a material approved for treatment of patients exposed to radioactive/nonradioactive cesium and/or thallium by the Food and Drug Administration (FDA).

In addition, the albumin included in the shell is the most abundant protein in a serum and is a surface stabilizer. Specifically, the albumin included in the shell may include bovine serum albumin (BSA) or human serum albumin (HSA). The albumin according to the present invention enables clinical use of the nanoparticles by improving stability of the nanoparticles and allows quick dispersion of the nanoparticles into a living body upon intravenous administration of the nanoparticles.

Prussian blue is mixed with the albumin in a molar ratio of 10:1 to 100:1, preferably 20:1 to 80:1. If the molar ratio of the Prussian blue to the albumin is less than the lower limit set forth above, the nanoparticles may not be stabilized, and if the molar ratio of the Prussian blue to the albumin is greater than the upper limit set forth above, sizes of the nanoparticles are not reduced any more. In addition, when the Prussian blue dye and the albumin are present in the molar ratio set forth above, there is no problem in impregnation of the near-infrared fluorescent dye.

The nanoparticles having a core-shell structure according to the present invention are more rapidly distributed in a living body and can emit a stronger signal by effective accumulation thereof in tumor tissue than nanoparticles having a plate shape or the like instead of a core-shell structure.

Further, the near-infrared fluorescent dye impregnated into the albumin layer may be any near-infrared fluorescent dye without limitation so long as the near-infrared fluorescent dye is strongly bonded to the albumin in a non-covalent manner and allows a signal thereof to be sensed by a near-infrared fluorescence imaging apparatus. The near-infrared fluorescent dye includes at least one selected from the group consisting of indocyanine green (ICG), Cy3.5, Cy5, Cy5.5, Cy7, cypate, and methylene blue, preferably indocyanine green (ICG).

When the near-infrared fluorescent dye is indocyanine green or methylene blue, the near-infrared fluorescent dye and the Prussian blue dye enable photodynamic therapy by generating reactive oxygen species as well as photothermal therapy, when irradiated with a near-infrared laser beam. In addition, the nanoparticles exhibit improved stability with respect to near-infrared light.

The near-infrared fluorescent dye is present in an amount of 60 wt % or less, preferably 1 wt % to 50 wt %, more preferably 10 wt % to 20 wt %, in the nanoparticles. If the amount of the near-infrared fluorescent dye is less than the lower limit set forth above, the nanoparticles can emit weak fluorescence signals and have an insignificant photothermal-photodynamic effect, and if the amount of the near-infrared fluorescent dye is greater than the upper limit set forth above, the nanoparticles cannot diagnose the presence or absence of a tumor and a position of the tumor since fluorescence signals are reduced by aggregation between fluorescent dye molecules.

Since the nanoparticles according to the present invention are minimally accumulated in major organs, for example, non-tumor sites, and are mainly accumulated in tumor sites, the nanoparticles exhibit fluorescence signals at a tumor site, which are 2 or more times, preferably 2 times to 5 times, that at a non-tumor site when the fluorescence signals are quantitatively analyzed.

Furthermore, the nanoparticles according to the present invention can be freeze-dried without antifreezing agents, and use of the nanoparticles is facilitated since the nanoparticles can be easily redispersed in all solutions and do not agglomerate upon redispersion.

The present invention also provides a method of diagnosing or treating an in vivo tumor of mammals except humans.

According to the present invention, a method of diagnosing or treating an in vivo tumor of mammals except humans includes: (A) injecting the nanoparticles as set forth above into a living body or specimen of mammals except humans; and (B) diagnosing the presence or absence of a tumor and a position of the tumor by sensing a signal emitted from the injected nanoparticles.

In operation (B), the signal emitted from the nanoparticles may be sensed by a nuclear magnetic resonance imaging apparatus and a near-infrared fluorescence imaging apparatus 5 hours to 25 hours after injection of the nanoparticles. If the residence time after injection of the nanoparticles is less than the lower limit set forth above, accuracy of diagnosis can be deteriorated since the signal is not strongly emitted from tumor tissue, and if the residence time after injection of the nanoparticles is greater than the upper limit set forth above, time is wasted since the signal does not become any stronger.

In addition, when the nanoparticles are accumulated in tumor tissue 5 hours to 25 hours after injection of the nanoparticles, only the tumor tissue is selectively necrotized by irradiating with a near-infrared laser beam. Specifically, when the nanoparticles (Prussian blue-albumin) having a core-shell structure, in which the surface of the Prussian blue dye is coated with the albumin, are injected and then irradiated with a near-infrared laser beam, the temperature of a tumor is increased to 45° C. or more, preferably 45° C. to 90° C., thereby partially necrotizing the tumor; and when the nanoparticles (Prussian blue-albumin-fluorescent dye), in which the albumin of the Prussian blue-albumin is impregnated with the near-infrared fluorescent dye, are injected and then irradiated with a near-infrared laser beam, the temperature of a tumor is increased to 45° C. or more, preferably 55° C. to 90° C., and reactive oxygen species are generated, thereby completely necrotizing the tumor.

Hereinafter, some examples of the present invention will be described in detail with reference to the accompanying drawings.

Control Group

A saline solution was used.

Example 1: Prussian Blue-Albumin Nanoparticles 10 mmol of each of $K_3Fe(CN)_6$ and $FeCl_2$ (Sigma-Aldrich Co. Ltd.) was freshly prepared in deionized water (DIW).

Next, a certain volume of the $K_3Fe(CN)_6$ solution was added into 1 ml of an aqueous solution of bovine serum albumin (BSA, Mw about 66 kD, Sigma-Aldrich Co. Ltd.) (5 mg/ml), followed by stirring the mixed solution at room temperature for 30 minutes. Next, a certain volume of the deionized water containing $FeCl_2$ was added to the mixture, followed by stirring at room temperature for 30 minutes, thereby forming blue-colored PB-BSA nanoparticles. Various concentrations of iron salts were used to confirm effects of ratios of iron concentrations to sizes of the PB-BSA nanoparticles. After reaction, unreacted salts and albumin were removed by spin filtration at 5000 rpm at room temperature for 10 minutes using Nanosep centrifugal devices (molecular weight 300 kD). These processes were repeated three times, thereby increasing purity of the nanoparticles.

Example 2: PB-BSA-ICG or PB-BSA-MB Nanoparticles

Indocyanine green (Sigma-Aldrich Co. Ltd.) (1 mg/ml) was added to the PB-BSA nanoparticles produced in Example 1, followed by mixing at room temperature under shaking conditions for 1 hour, thereby forming PB-BSA-ICG nanoparticles. Next, unbound ICG molecules were separated by spin filtration, and loading amount of indocyanine green was measured by absorbance measurement in a spectrophotometer.

Methylene blue (Sigma-Aldrich Co. Ltd.) (1 mg/ml) was added to the PB-BSA nanoparticles produced in Example 1, followed by mixing at room temperature for 1 hour, thereby forming PB-BSA-MB nanoparticles. Unbound MB molecules were separated by spin filtration, and loading amount was measured by absorbance measurement.

Comparative Example 1

Indocyanine green (ICG) and Methylene blue (MB) was used.

Figure 1B:
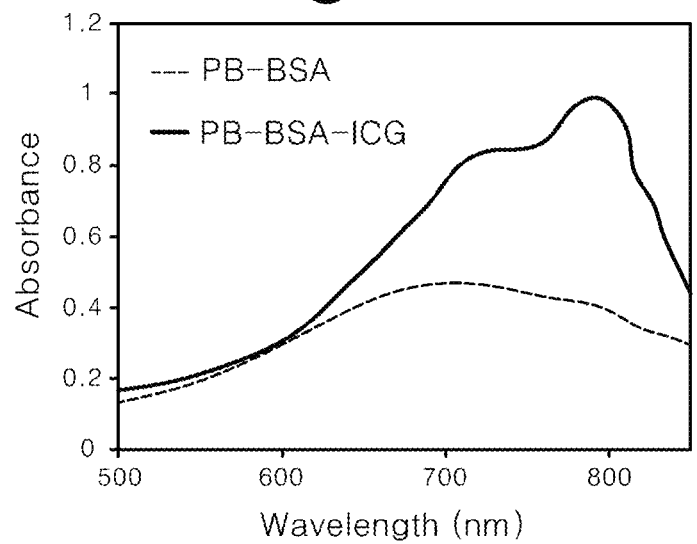
FIG. 1b shows absorption spectra of the PB-BSA nanoparticles and the PB-BSA-ICG nanoparticles.
Figure 1C:
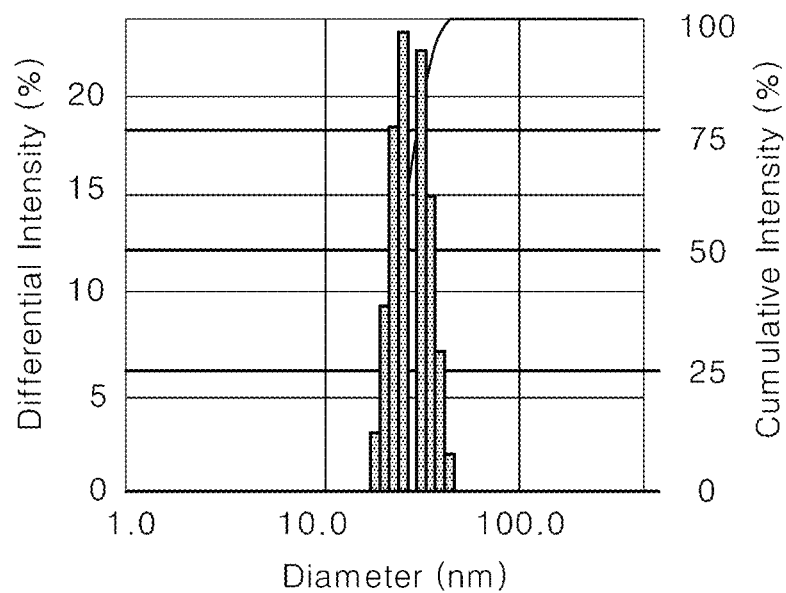
FIG. 1c is a size distribution map of the PB-BSA-ICG nanoparticles treated with DLS.

FIG. 1a shows schematic diagrams of the PB-BSA nanoparticles produced in Example 1 and the PB-BSA-ICG or PB-BSA-MB nanoparticles produced in Example 2; FIG. 1b shows absorption spectra of the PB-BSA nanoparticles and the PB-BSA-ICG nanoparticles; and FIG. 1c is a size distribution map of the PB-BSA-ICG nanoparticles treated with DLS.

Figure 2A:
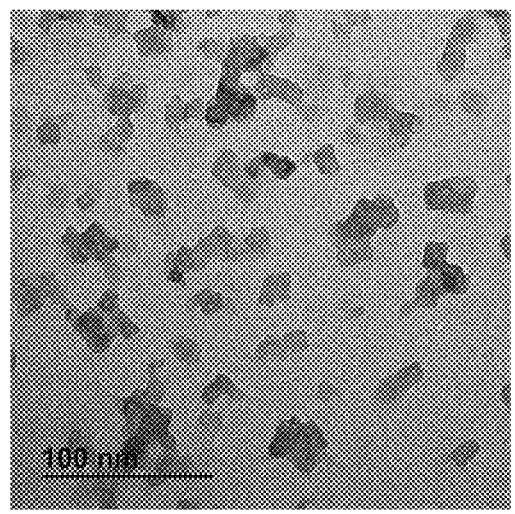
FIG. 2a shows transmission electron microscope (TEM) images of the PB-BSA-ICG nanoparticles of Example 2.
Figure 2B:
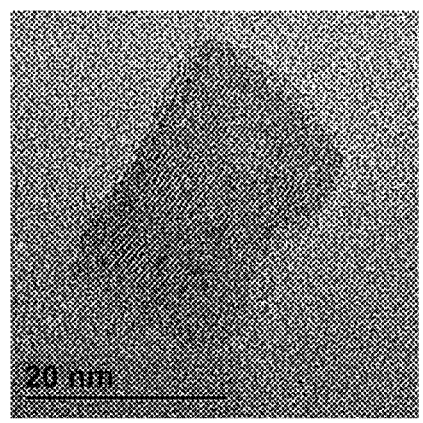
FIG. 2b shows the high resolution TEM image of a single PB-BSA-ICG nanoparticles of Example 2.
Figure 3A:
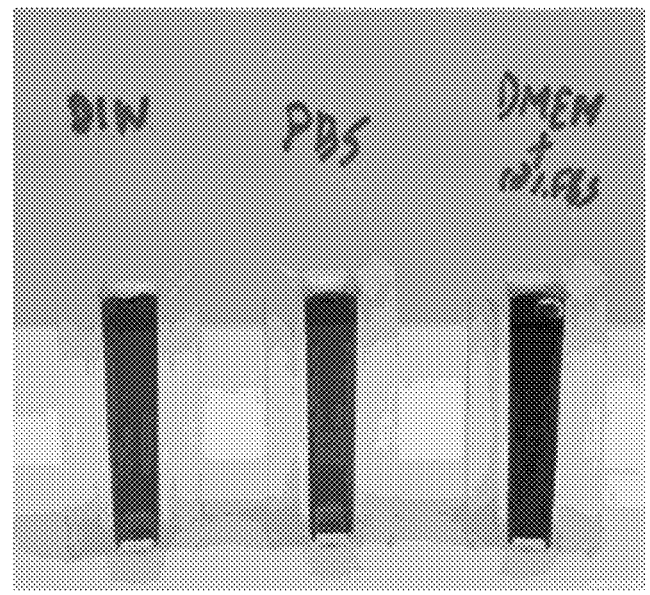
FIG. 3a is a picture showing redispersion of freeze-dried PB-BSA nanoparticles in various media such as DIW, PBS, and DMEM (DMEM+10% FBS), respectively.
Figure 3B:
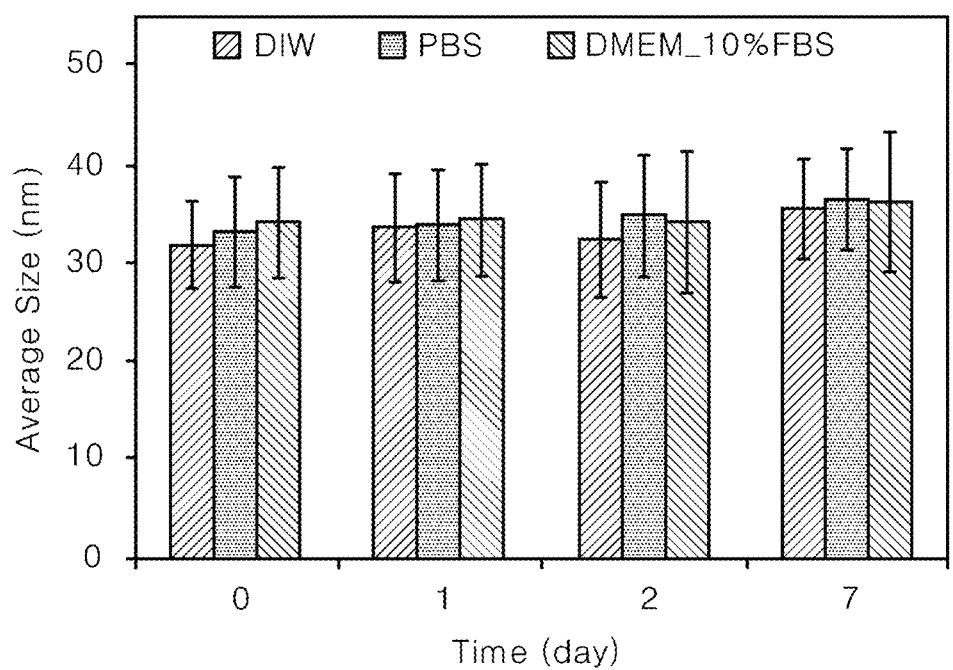
FIG. 3b is a graph depicting stability of PB-BSA nanoparticles by measuring size change over time in various media such as DIW, PBS, and DMEM (DMEM+10% FBS), respectively.

FIG. 2a shows transmission electron microscope (TEM) images of the PB-BSA-ICG nanoparticles of Example 2; FIG. 2b shows the high resolution TEM image of a single PB-BSA-ICG nanoparticles of Example 2; FIG. 3a is a picture showing redispersion of freeze-dried PB-BSA nanoparticles in various media such as DIW, PBS, and DMEM (DMEM+10% FBS), respectively; and FIG. 3b is a graph depicting stability of PB-BSA nanoparticles by measuring size change over time in various media such as DIW, PBS, and DMEM (DMEM+10% FBS), respectively.

Figure 4:
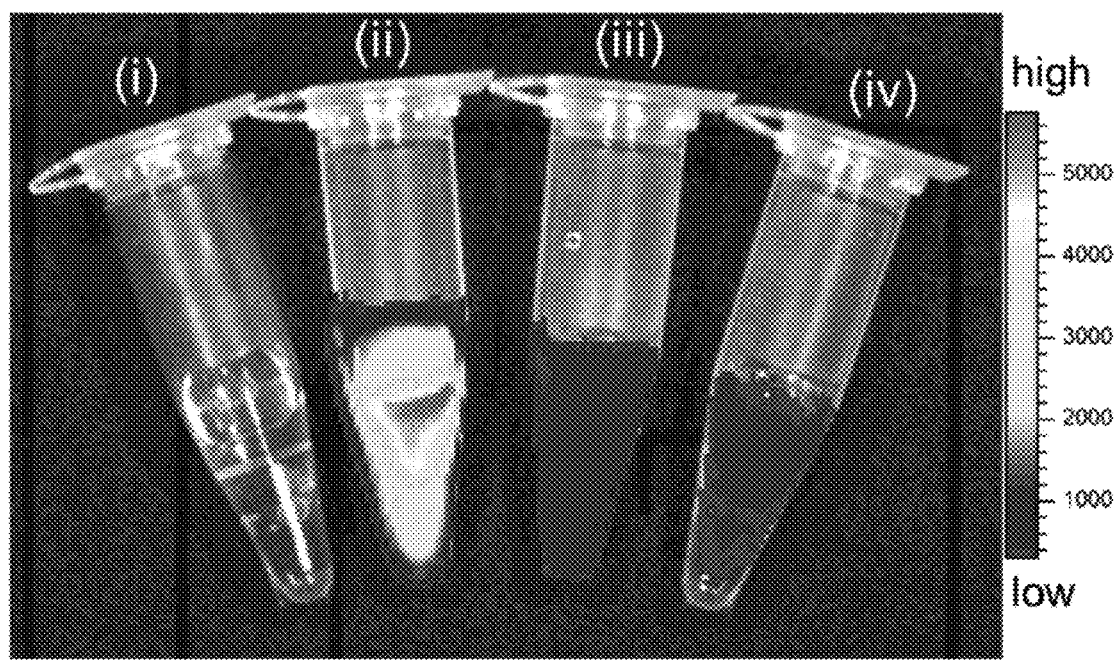
FIG. 4 shows NIR fluorescence signals of (i) PBS, (ii) PB-BSA-ICG 10, (iii) PB-BSA-ICG 25, and (iv) PB-BSA-ICG 50 solutions, respectively.

Further, FIG. 4 shows NIR fluorescence signals of (i) PBS, (ii) PB-BSA-ICG 10, (iii) PB-BSA-ICG 25, and (iv) PB-BSA-ICG 50 solutions.

The nanoparticles for diagnosis or treatment of tumors according to the present invention may include: core-shell structured nanoparticles (PB-BSA nanoparticles), in which a surface of a Prussian blue (PB) dye is coated with bovine serum albumin (BSA), as produced in Example 1; and nanoparticles, in which indocyanine green (ICG) is impregnated into an albumin layer corresponding to a shell of the core-shell structured nanoparticles, as produced in Example 2 (FIG. 1a).

The average particle size of the PB-BSA nanoparticles varies with concentration of iron salts and a ratio of albumin to $Fe^{2+}/Fe^{3+}$, and this is shown in Table 1.

TABLE 1

| $Fe^{2+}/Fe^{3+}$ (mmol) | Albumin (mmol) | Albumin:$Fe^{2+}/Fe^{3+}$ ratio | Size (nm) | Zeta potential (mV) |
| --- | --- | --- | --- | --- |
| 0.5 | 0.075 | 1:6.67 | 31 ± 9 | −16 ± 3 |
| 1 | 0.075 | 1:13.33 | 56 ± 12 | −18 ± 3 |
| 2 | 0.075 | 1:26.67 | 98 ± 14 | −19 ± 2 |

As shown in Table 1, when 0.5 mmol of $Fe^{2+}/Fe^{3+}$ and 0.075 mmol of albumin (BSA) were used, the nanoparticles having an average particle diameter of 31 nm as measured by DLS were produced. It was confirmed that the average particle diameter of the PB-BSA nanoparticles was increased from 31 nm to 98 nm when the amount of the Fe salt was increased from 0.5 mmol to 2 mmol and the ratio of the albumin to $Fe^{2+}/Fe^{3+}$ was increased from 1:6.67 to 1:26.67. In addition, it was confirmed that the zeta potential of the PB-BSA nanoparticles ranged from −16 mV to −19 mV.

Since nanoparticles having small sizes are more effective for application to theranostics, subsequent experiments were performed using the PB-BSA nanoparticles having an average particle diameter of 31 nm.

It was confirmed that the PB-BSA nanoparticles exhibited a peak at a wavelength of about 710 nm and a broad absorption spectrum at a wavelength of 500 nm to 850 nm (FIG. 1b), and it was confirmed by electron microscopy (TEM) that the PB-BSA nanoparticles were cubical shape with an average particle size of about 20 nm (FIG. 2). Since measurement using TEM was performed by drying a drop of a PB-BSA nanoparticle solution on a copper grid surface, the average particle diameter of the PB-BSA nanoparticles measured using TEM was less than that measured using DLS.

For stability analysis, it was confirmed that the purified PB-BSA nanoparticles could be freeze-dried without antifreezing agents, and easily redispersed using deionized water (DIW), a phosphate buffer solution (PBS, 0.1 M, pH 7.4) and a 10% FBS-containing cell culture medium (DMEM+10% FBS) and did not suffer from agglomeration. The freeze-dried PB-BSA nanoparticles were stable for 7 days or more without significant size change (FIG. 3).

Since, ICG and MB has great affinity towards albumin, it was easily impregnated into the albumin layer of the PB-BSA nanoparticles by simply mixing.

As such, in the produced PB-BSA-ICG or PB-BSA-MB nanoparticles of Example 2, the amount of impregnated ICG or MB could be increased by increasing the amount of ICG or MB during mixing process, and this result is shown in Table 2.

TABLE 2

| Item | ICG (µg) | Encapsulation efficiency (%) | Impregnation concentration (%) |
| --- | --- | --- | --- |
| PB-BSA-ICG 10 | 10 | 100 | 12.5 |
| PB-BSA-ICG 25 | 25 | 94.4 | 29.5 |
| PB-BSA-ICG 50 | 50 | 92.6 | 57.9 |
| PB-BSA-MB 10 | 10 | 97.8 | 12.2 |
| PB-BSA-MB 25 | 25 | 89.1 | 27.8 |
| PB-BSA-MB 100 | 50 | 81.7 | 51.1 |

As shown in Table 2, the impregnation concentration of ICG or MB could be increased to 57.9% or 51.1% respectively, due to strong interaction between ICG or MB and the serum albumin.

The PB-BSA-ICG nanoparticles had a problem of reduction in fluorescence signals with increasing impregnation concentration of ICG, and provided excellent fluorescence signals at an impregnation concentration of ICG of 12.5% as a measurement result using IVIS imaging (FIG. 4).

It was confirmed that the PB-BSA-ICG nanoparticles had a clearly observed absorption peak at a wavelength of about 785 nm (FIG. 1b), an average particle diameter of 33 nm±5 nm as measured by DLS (FIG. 1c), and a zeta potential of −17 mV±5 mV.

Figure 5A:
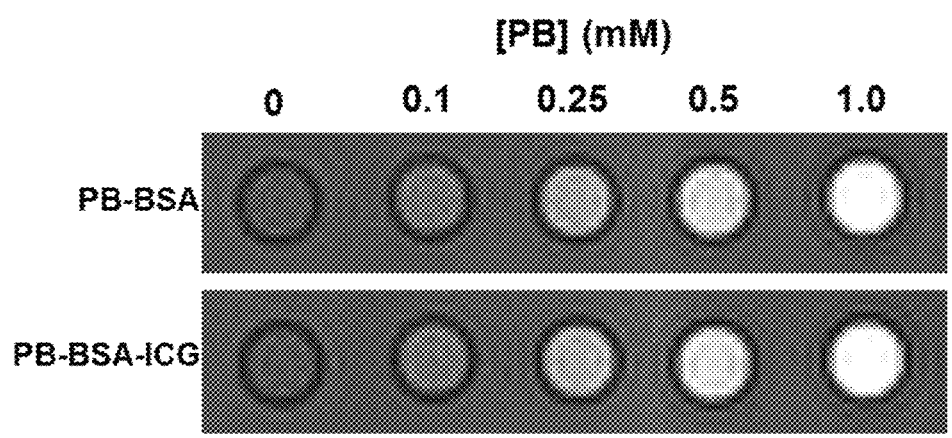
FIG. 5a is a T1-weighted MR image of PB-BSA and PB-BSA-ICG nanoparticles in which concentrations of PB is gradually increased.
Figure 5B:
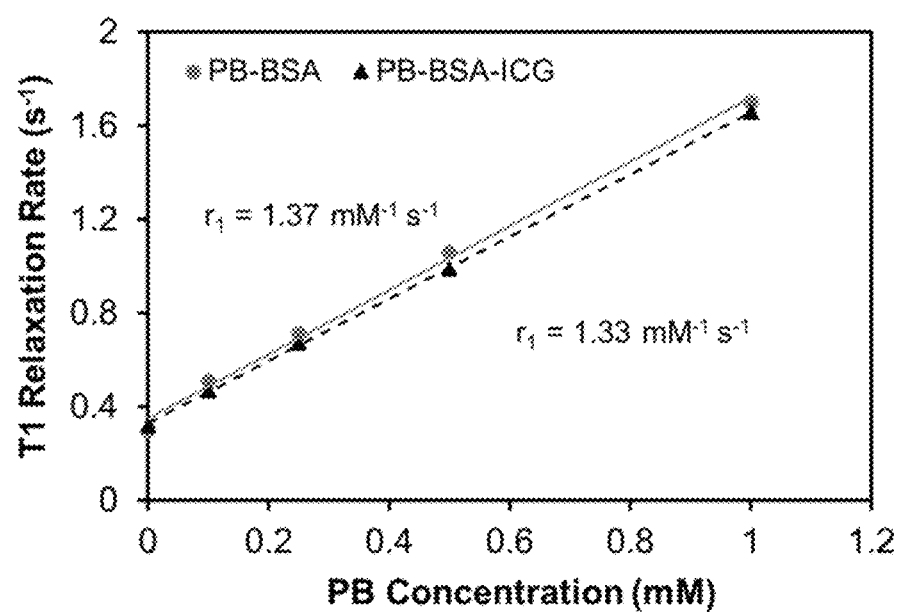
FIG. 5b is a plot of T1 relaxation rate vs. PB concentration for PB-BSA and PB-BSA-ICG nanoparticles.

FIG. 5a is a T1-weighted MR image of PB-BSA and PB-BSA-ICG nanoparticles in which concentrations of PB is gradually increased, and FIG. 5b is a plot of T1 relaxation rate vs. PB concentration for PB-BSA and PB-BSA-ICG nanoparticles.

Since Prussian blue (PB) has a capability of reducing longitudinal and transverse relaxation times (T1 and T2) of a proton from water, T1- or T2-weighted MR imaging can be used.

In diagnosis, however, since T1-weighted MR imaging is more suitable for clinical medicine than T2-weighted MR imaging, characteristics of T1-weighted MR images of the PB-BSA nanoparticles were focused.

A T1-based contrast agent reduces longitudinal and transverse relaxation times of protons from water and gives a positive signal brightening a region in which the T-based contrast agent is present.

The PB-BSA nanoparticles of Example 1 having different concentrations were analyzed with respect to T1-weighted MR signals using a 3T clinical MRI system. As a result, concentration-dependent increase and brightening effects were clearly observed in T1-weighted signals (FIG. 5a)

Further, the PB-BSA and PB-BSA-ICG nanoparticles had a longitudinal relaxation (rl) of about 1.37 $mM^{-1}s^{-1}$ and 1.33 $mM^{-1}s^{-1}$ respectively, as measured using a slope of a plot of 1/T1 vs. PB concentration (FIG. 5b). Typically, it was reported that PEGylated PB nanoparticles had an rl value of 6.4 $mM^{-1}s^{-1}$ when a 9.4T small animal MRI system (L. Cheng, H. Gong, W. Zhu, J. Liu, X. Wang, G. Liu, Z. Liu, *Biomaterials* 2014, 35, 9844.). Although this value is better than the measured longitudinal relaxation (rl) of the PB-BSA nanoparticles, since the PB-BSA nanoparticles provide more effective targeting at tumor tissue and excellent accumulation in cells in terms of size, the PB-BSA nanoparticles allow more efficient MRI images to be obtained. Further, Magnevist (gadolinium diethylenetriamine pentaacetic acid, Bayer Healthcare Pharmaceuticals), which is a clinically used T1 contrast agent, has a higher rl value of 4.3 $mM^{-1}s^{-1}$ than the PB-BSA nanoparticles (M. F. Dumont, H. A. Hoffman, P. R. S. Yoon, L. S. Conklin, S. R. Saha, J. Paglione, R. W. Sze, R. Fernandes, *Bioconjug. Chem.* 2014, 25, 129).

Figure 5C:
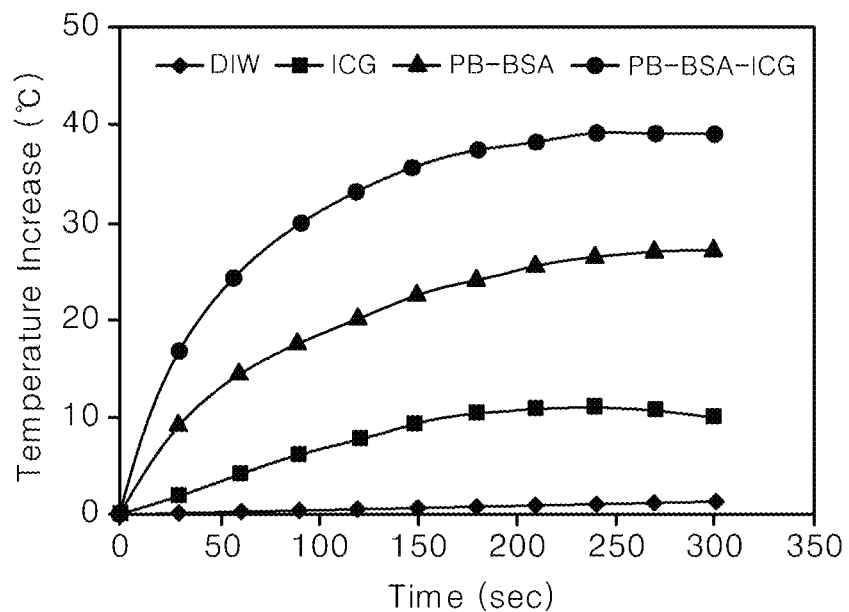
FIG. 5c is a graph depicting photothermal stability of each of a control group, free ICG, PB-BSA nanoparticles, and PB-BSA-ICG nanoparticles upon NIR laser irradiation.
Figure 5D:
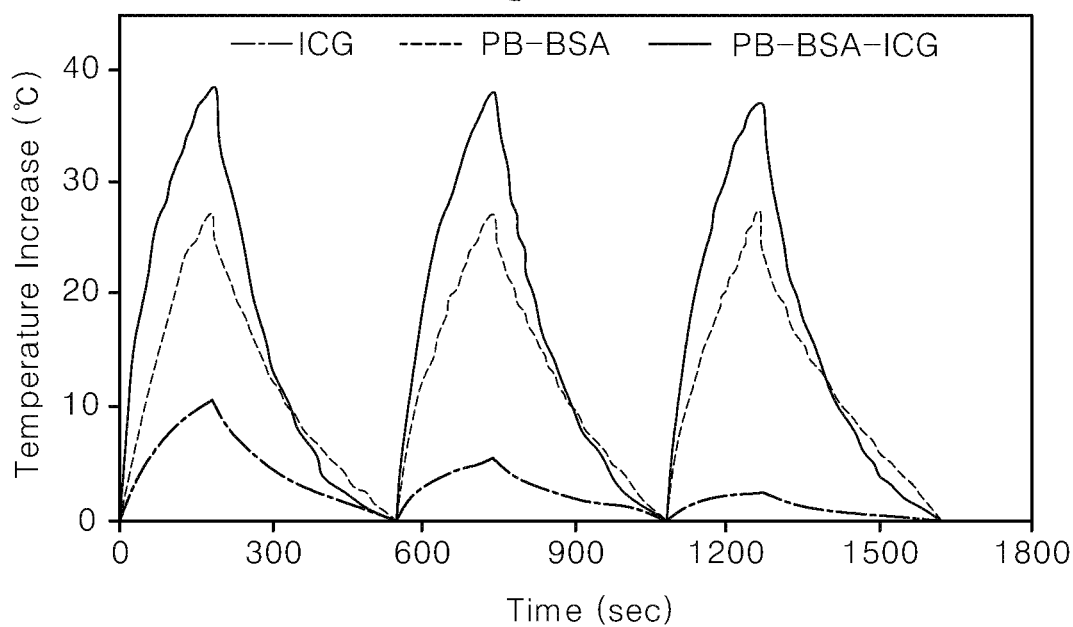
FIG. 5d is a graph depicting photothermal stability of each of a control group, free ICG, PB-BSA nanoparticles, and PB-BSA-ICG nanoparticles upon repeated NIR laser irradiation.

FIG. 5c is a graph depicting photothermal stability of each of a control group, free ICG (Comparative Example 1), PB-BSA nanoparticles (Example 1), and PB-BSA-ICG nanoparticles (Example 2) upon NIR laser irradiation (1 W/cm$^2$), and FIG. 5d is a graph depicting photothermal stability of each of a control group, free ICG (Comparative Example 1), PB-BSA nanoparticles (Example 1), and PB-BSA-ICG nanoparticles (Example 2) after repetition of NIR laser irradiation (1 W/cm$^2$) for 3 cycles (laser irradiation for 3 minutes per cycle)

Photothermal properties of the PB-BSA nanoparticles and the PB-BSA-ICG nanoparticles were investigated using a continuous wave NIR laser (808 nm, 1 W/cm$^2$).

After laser irradiation for 8 minutes, a PB-BSA nanoparticle solution (80 µg/ml) and a free ICG solution (10 µg/ml) exhibited temperature increases of 27° C. and 10° C., respectively, and a PB-BSA-ICG nanoparticle solution exhibited a higher temperature increase of 39° C. than the PB-BSA nanoparticle solution or the free ICG solution (FIG. 5c). The significant temperature increase suggests cooperated photothermal activities of the PB-BSA nanoparticles and ICG, and photothermal stability was analyzed by exposing the free ICG solution, the PB-BSA nanoparticle solution and the PB-BSA-ICG nanoparticle solution to repeated cycles of laser irradiation.

Photothermal efficiency of the free ICG solution (10 µg/ml) was significantly reduced in each cycle. Specifically, the temperature increase of the free ICG solution was about 10° C. for a first cycle, was reduced to about 6° C. for a second cycle, and became 2.5° C. for a third cycle (FIG. 5d). This result is caused by instability and degradation of ICG molecules due to repeated laser irradiation.

However, since the PB-BSA nanoparticle solution and the PB-BSA-ICG nanoparticle solution exhibited constant temperature increases of 27° C. and 39° C. for each cycle, excellent photothermal stability of the PB-BSA nanoparticle solution and the PB-BSA-ICG nanoparticle solution was confirmed.

It was confirmed that photothermal stability of ICG of the PB-BSA-ICG nanoparticle solution was improved, and that there was no deterioration in photothermal efficiency of the PB-BSA-ICG nanoparticle solution after the third cycle of laser irradiation (FIG. 5d).

Figure 6A:
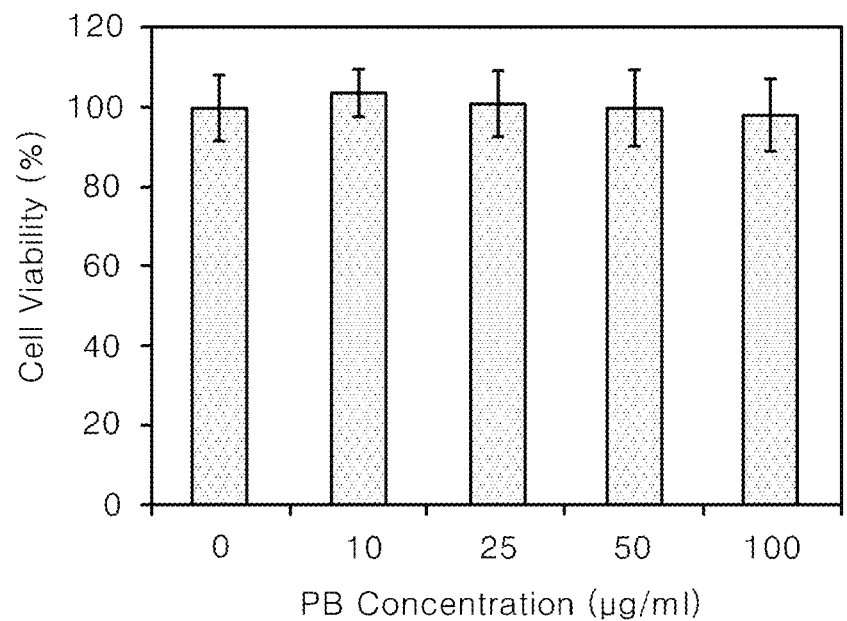
FIG. 6a is a graph depicting viability of cancer cells (SCC7) after treatment with PB-BSA nanoparticles having various concentrations for 24 hours.

FIG. 6 shows results of in vitro experiments, in which FIG. 6a is a graph depicting viability of cancer cells (SCC7) after treatment with PB-BSA nanoparticles having various concentrations for 24 hours; FIG. 6b is a graph depicting an effect of phototherapy of each of free ICG, PB-BSA nanoparticles, and PB-BSA-ICG nanoparticles after NIR laser irradiation (1 W/cm$^2$, 5 minutes) of 80 µg/ml of PB and 10 µg/ml of ICG; FIG. 6c is a graph depicting cellular uptake of each of free ICG and PB-BSA-ICG nanoparticles into SCC7 cells after culture for 24 hours, as analyzed by flow cytometry; FIG. 6d is a graph depicting average fluorescence intensity of each of free ICG and PB-BSA-ICG nanoparticles, as measured by flow cytometry of cellular uptake (n=4); and FIG. 6e shows NIR light induced intracellular singlet oxygen ($^1O_2$) generated in each of free ICG and PB-BSA-ICG nanoparticles using a H2DCF-DA dye emitting green fluorescence, after intracellular oxidation occurring due to a PDT effect of ICG.

Toxicity of the PB-BSA nanoparticles was evaluated using squamous carcinoma (SCC7) cells.

It was confirmed that cell viability was 100% for the PB-BSA nanoparticles having a PB concentration of 10 µg/ml and 98% for the PB-BSA nanoparticles having a high PB concentration of 100 µg/ml (FIG. 6a).

Figure 6B:
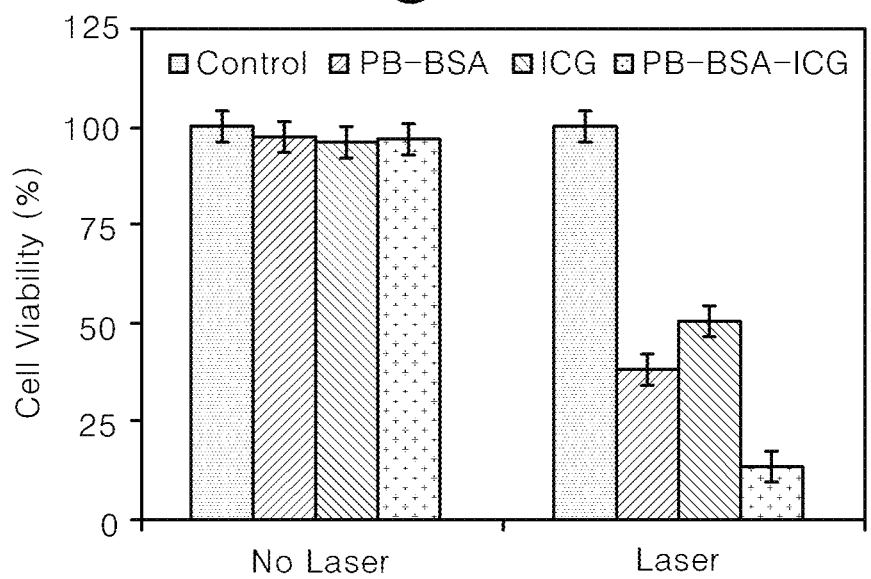
FIG. 6b is a graph depicting an effect of phototherapy using each of free ICG, PB-BSA nanoparticles, and PB-BSA-ICG nanoparticles after NIR laser irradiation.

In addition, in vitro phototherapy effects of free ICG, the PB-BSA nanoparticles, and the PB-BSA-ICG nanoparticles were compared using SCC7 cells, and cell viability without laser treatment was almost 100% for all of the groups, as expected (FIG. 6b). However, it was confirmed that cell viability after NIR laser irradiation (1 W/cm$^2$, 5 minutes) was reduced to 55% and 38% for free ICG and the PB-BSA nanoparticles, respectively. Further, it was confirmed that cell viability after NIR laser irradiation (1 W/cm$^2$, 5 minutes) was reduced to 13% for the PB-BSA-ICG nanoparticles. This means that the PB-BSA-ICG nanoparticles exhibited improved cytotoxicity due to phototherapy (FIG. 6b).

Cellular uptake of the PB-BSA-ICG nanoparticles was quantitatively analyzed by flow cytometry and was compared by uptake of free ICG.

Figure 6C:
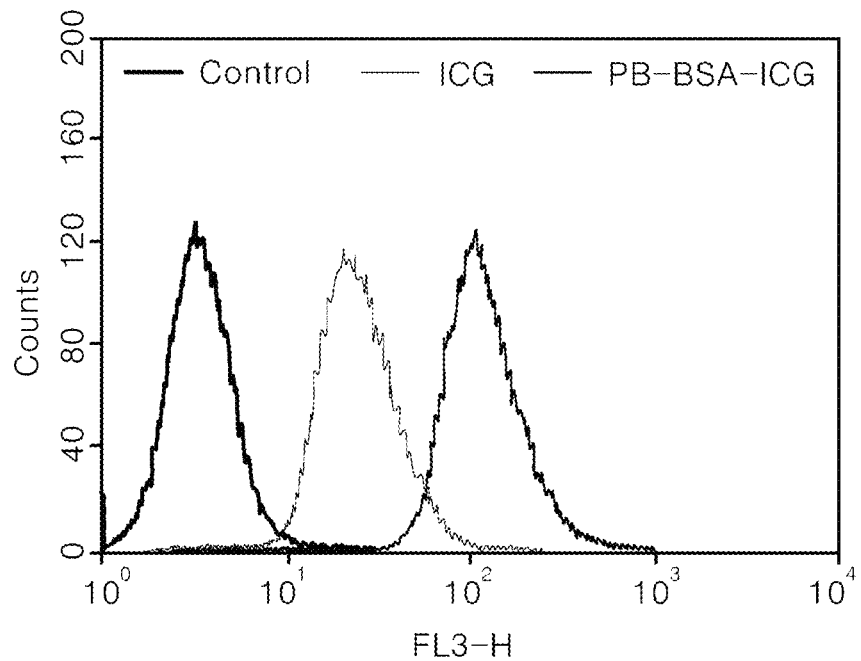
FIG. 6c is a graph depicting cellular uptake of each of free ICG and PB-BSA-ICG nanoparticles into SCC7 cells after culture for 24 hours, as analyzed by flow cytometry.
Figure 6D:
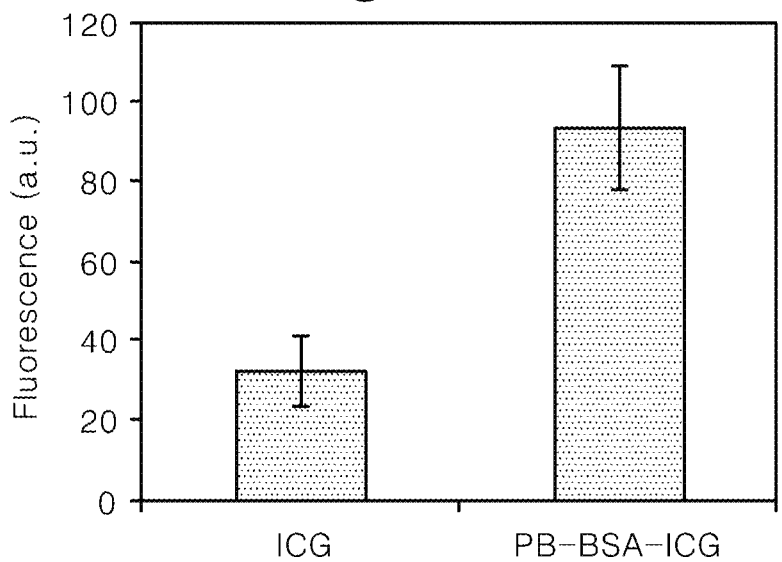
FIG. 6d is a graph depicting average fluorescence intensity of each of free ICG and PB-BSA-ICG nanoparticles, as measured by flow cytometry of cellular uptake.

Cell-related NIR fluorescence was observed after culture of free ICG or the PB-BSA-ICG nanoparticles for 24 hours, and high fluorescence signals in cells treated with the PB-BSA-ICG nanoparticles mean improved cellular uptake as compared with free ICG (FIG. 6c). Quantitative analysis of flow data showed that fluorescence of cells cultured with the PB-BSA-ICG nanoparticles was 2.9 times fluorescence of cells cultured with free ICG (FIG. 6d).

Further, free ICG has photodynamic properties and can generate singlet oxygen ($^1O_2$) when exposed to an 808 nm NIR laser beam. Generation of intracellular singlet oxygen ($^1O_2$) was analyzed using 2',7'-dichlorodihydrofluorescein diacetate (H2DCF-DA) dye as a reactive oxygen species (ROS) probe.

After 808 nm laser irradiation, SCC7 cells treated with free ICG or the PB-BSA-ICG nanoparticles were cultured with H2DCF-DA and visualized by fluorescence microscopy.

Figure 6E:
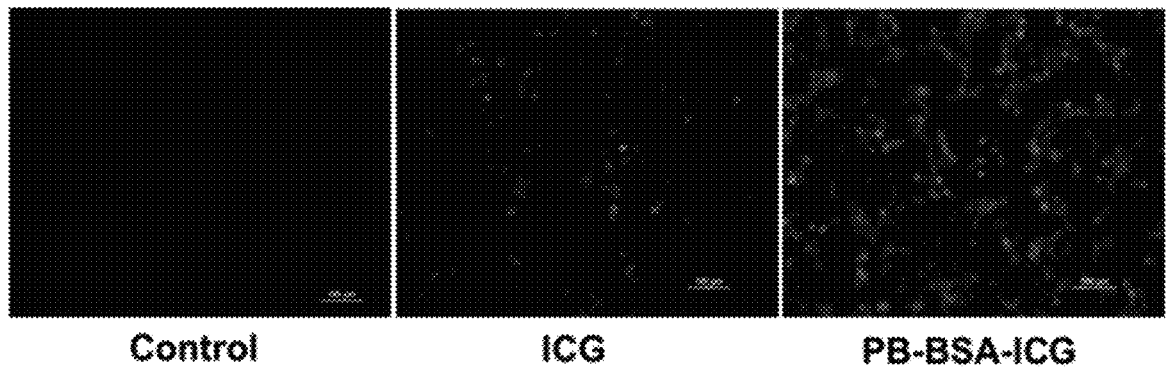
FIG. 6e shows NIR light induced intracellular singlet oxygen ($^1O_2$) generated in each of free ICG and PB-BSA-ICG nanoparticles using H2DCF-DA dye emitting green fluorescence, after intracellular oxidation due to a PDT effect of ICG.

Fluorescence signals were not observed in cells of a control group as they did not generate $^1O_2$ upon laser irradiation. But intracellular green fluorescence signals were observed in cells cultured with free ICG or the PB-BSA-ICG nanoparticles upon laser irradiation, confirming $^1O_2$ generation (FIG. 6e).

Green fluorescence signals generated from the cells treated with the PB-BSA-ICG nanoparticles was higher than those of the cells treated with free ICG due to high cellular uptake of the PB-BSA-ICG nanoparticles and this result means that ICG of the PB-BSA-ICG nanoparticles can generate $^1O_2$ by NIR laser irradiation.

Therefore, it can be concluded that higher cytotoxicity of the PB-BSA-ICG nanoparticles than that of free ICG or the PB-BSA nanoparticles after laser treatment is due to improved cellular uptake and a combined effect of PTT and PDT.

Figure 7A:
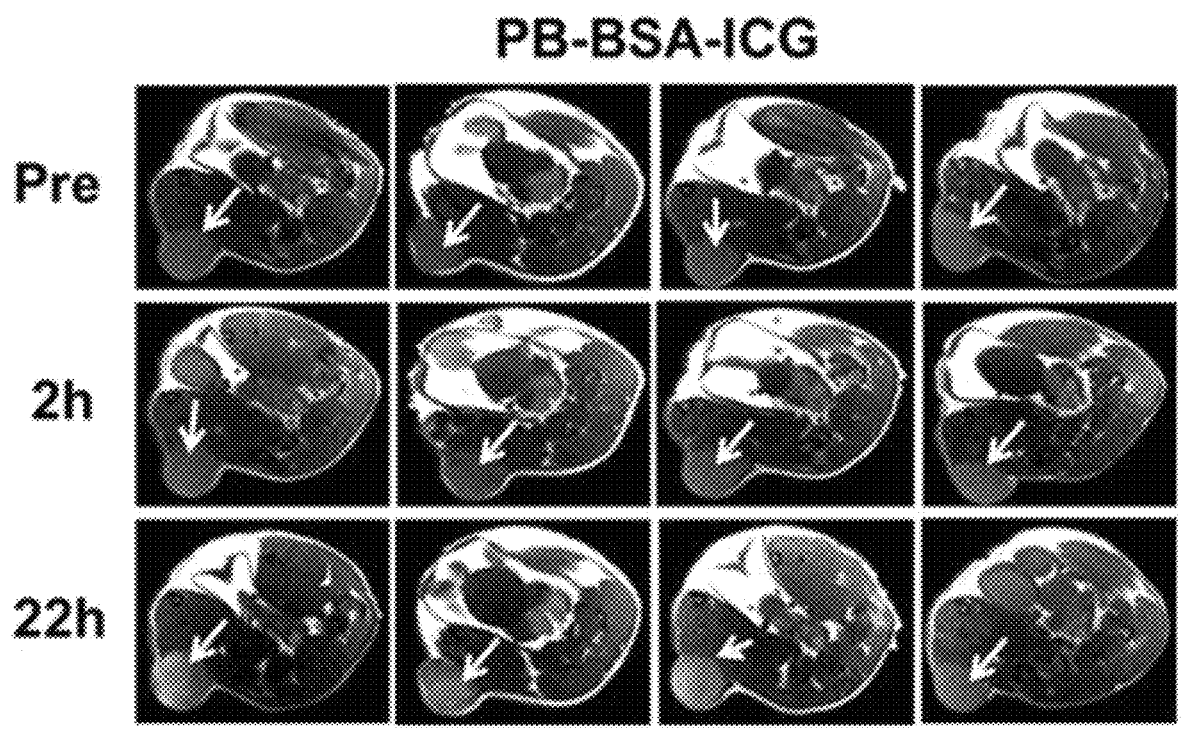
FIG. 7a shows pictures showing time-dependent brightness of tumor sites by T1-weighted MR signals generated due to PB-BSA-ICG nanoparticles.
Figure 7B:
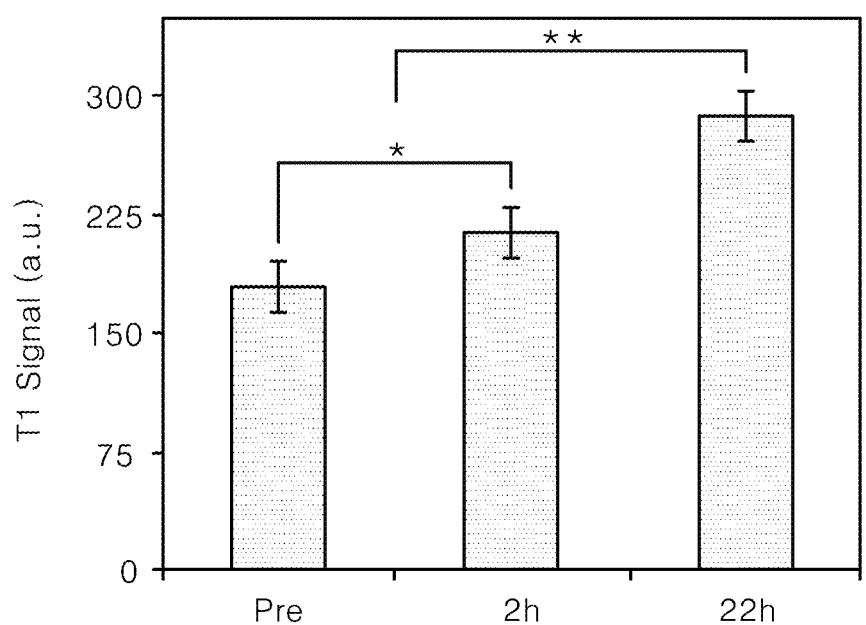
FIG. 7b is a graph depicting results of quantitative analysis of changes in T1-weighted MR signals in tumor sites.

FIGS. 7a to 7b are related to T1-weighted in vivo MR images of tumor-xenograft mice (n=4) after intravenous infusion of the PB-BSA-ICG nanoparticles; FIG. 7a shows pictures showing time-dependent brightness of tumor sites by T1-weighted MR signals generated due to PB-BSA-ICG nanoparticles (tumors are indicated by arrows); and FIG. 7b is a graph depicting results of quantitative analysis (n=4, *P>0.05, **P<0.05) of changes in T1-weighted MR signals in tumor sites.

Figure 8A:
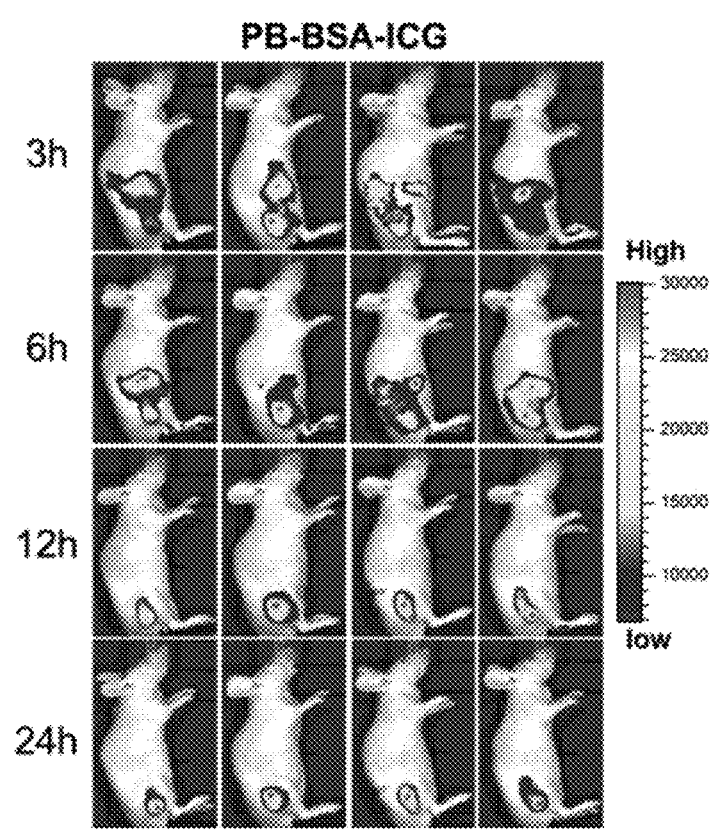
FIG. 8a shows in vivo NIR fluorescence images of athymic mice upon intravenous infusion of PB-BSA-ICG nanoparticles.
Figure 8B:
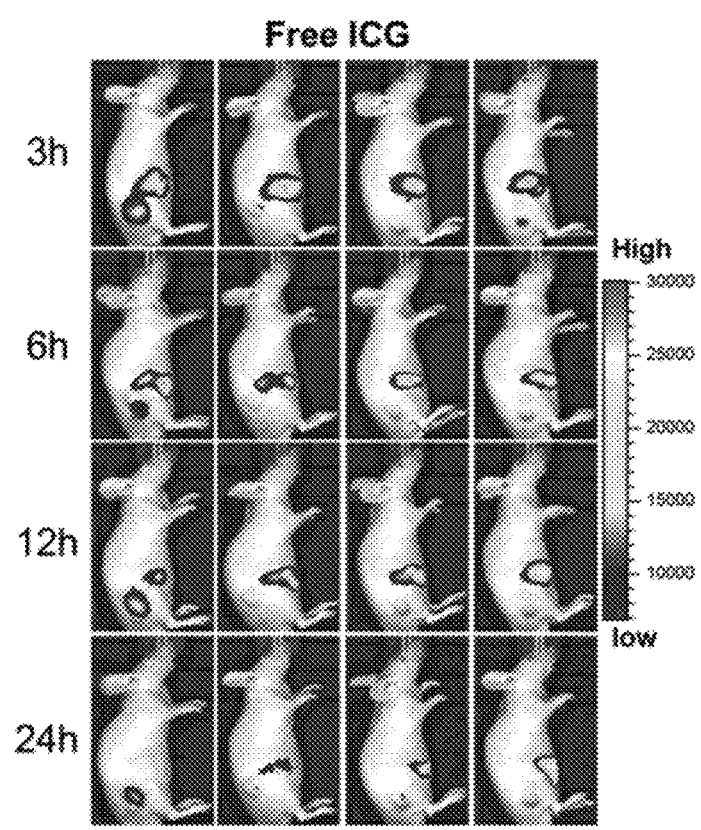
FIG. 8b shows in vivo NIR fluorescence images of athymic mice upon intravenous infusion of a free ICG solution.

FIG. 8a shows in vivo NIR fluorescence images of athymic mice (n=4) upon intravenous infusion of the PB-BSA-ICG nanoparticles; and FIG. 8b shows in vivo NIR fluorescence images of athymic mice (n=4) upon intravenous infusion of a free ICG solution.

Figure 9A:
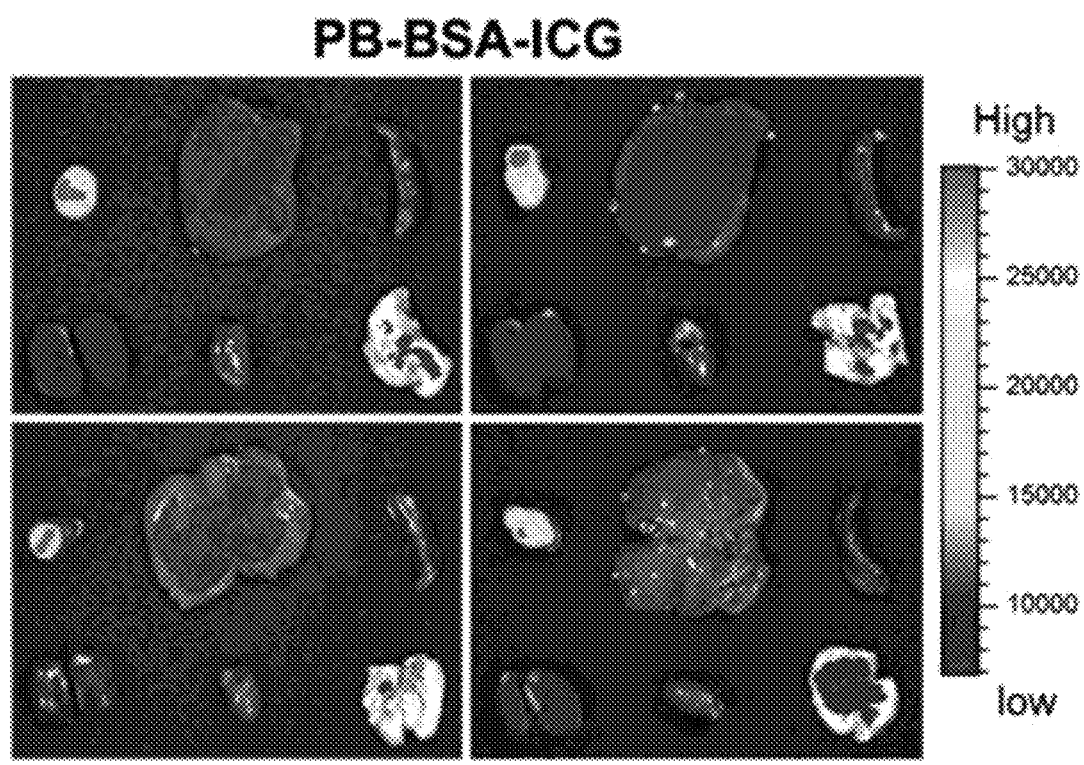
FIG. 9a shows ex vivo fluorescence images of major organs and tumors resected from sacrificed mice 24 hours after injection of a PB-BSA-ICG nanoparticle solution.
Figure 9B:
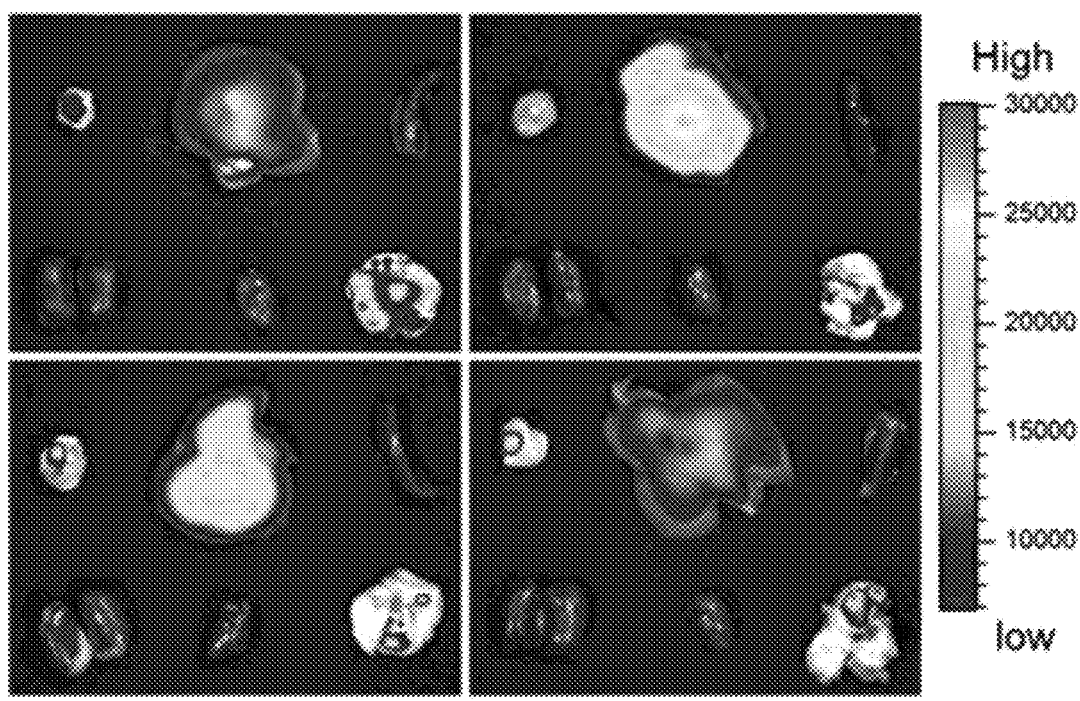
FIG. 9b shows ex vivo fluorescence images of major organs and tumors resected from sacrificed mice 24 hours after injection of a free ICG solution.
Figure 9C:
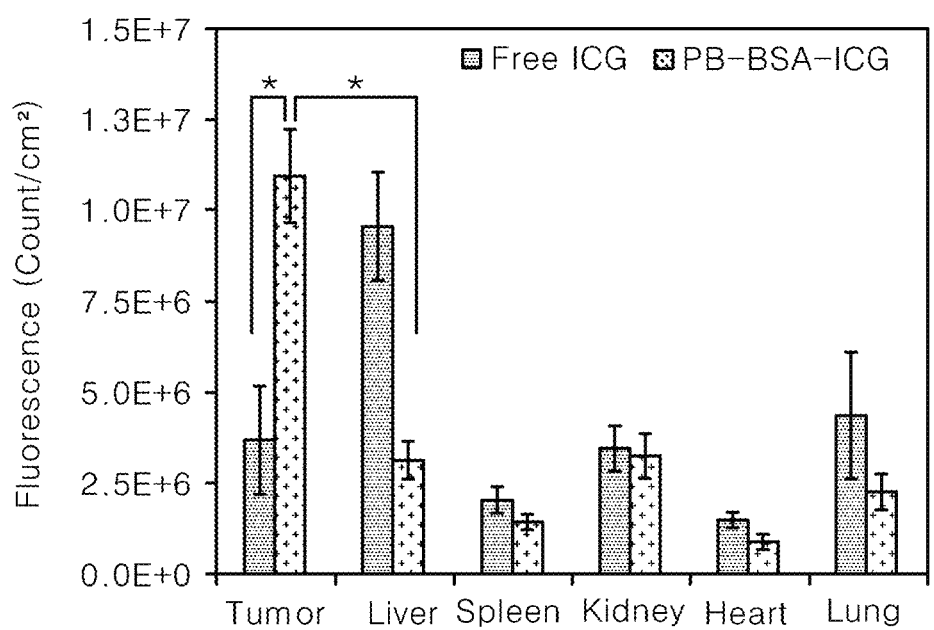
FIG. 9c is a graph depicting fluorescence intensity of major organs and tumors 24 hours after injection of each of PB-BSA-ICG nanoparticle and free ICG solutions.

Further, FIG. 9a shows ex vivo fluorescence images of major organs and tumors resected from sacrificed mice (n=4) 24 hours after injection of a PB-BSA-ICG nanoparticle solution; FIG. 9b shows ex vivo fluorescence images of major organs and tumors resected from sacrificed mice (n=4) 24 hours after injection of a free ICG solution (upper side: tumor, liver, spleen; lower side: kidney, heart, lung (from left to right)); and FIG. 9c is a graph depicting fluorescence intensity of major organs and tumors 24 hours after injection of each of the PB-BSA-ICG nanoparticles and the free ICG solutions (n=4, *P<0.01).

Potential application of the PB-BSA-ICG nanoparticles was evaluated in a mouse xenograft model using dual mode MR for in vivo tumor diagnosis and an optical imaging agent.

SCC7 tumor-containing mice (n=4) were subjected to intravenous administration of the PB-BSA-ICG nanoparticles (dosage of PB: 20 mg/kg, dosage of ICG: 2 mg/kg), and T1-weighted MR signals were obtained by a 3T clinical MRI scanner.

The same group of mice was investigated as to NIR fluorescence signals by an in vivo imaging system (IVIS).

T1-weighted MR signals in tumor regions were significantly changed over time, and, 2 hours after injection, slight increases in MR signals were observed in the tumor regions. However, after 22 hours, tumors looked much brighter than those in images taken before injection of the PB-BSA-ICG nanoparticles (FIG. 7a).

It was confirmed that T1-weighted MR signal intensity at a tumor site was increased by 1.2 times and 1.7 times 2 hours and 22 hours after injection, respectively (FIG. 7b).

It was confirmed that the PB-BSA nanoparticles could be preferentially accumulated into the tumor sites, and could generate sufficient T1-weighted MR signals for MR imaging. In addition, NIR fluorescence images were obtained by monitoring bio-distribution of the PB-BSA-ICG nanoparticles and tumor position measurement.

Although fluorescence signals were widely distributed in overall bodies including tumors at 3 hours and 6 hours after injection of the PB-BSA-ICG nanoparticles, strong fluorescence signals were observed only at the tumor sites in all the mice after 12 hours (FIG. 8a). In addition, it was confirmed that the tumor sites exhibited strong fluorescence signals at 24 hours (FIG. 8a).

The improved time-dependent fluorescence signals at the tumor sites coincided well with MR image data proving that the PB-BSA-ICG nanoparticles could be used for two different mode of imaging.

The free ICG solution (2 mg/kg) was injected into other mice as a control group for IVIS imaging. Free ICG injected into the mice exhibited strong signals at liver sites 3 hours after injection, and the strong signals were gradually reduced over time. Gradual reduction of the signals means that free ICG molecules were quickly discharged from the bodies of the mice (FIG. 8b).

The PB-BSA-ICG nanoparticles according to the present invention exhibited significantly strong signals at the tumor sites 24 hours after injection, suggesting long-term blood circulation and more effective tumor accumulation. The systemically administered nanoparticles due to long-term blood circulation can be accumulated in tumor tissue by an EPR effect which is a primary cause of high accumulation of the PB-BSA nanoparticles and the PB-BSA-ICG nanoparticles in the tumor sites.

24 hours after injection, all of the mice were sacrificed to collect major organs, and fluorescence signals were recorded to analyze bio-distribution of each of the PB-BSA-ICG nanoparticles and free ICG. As expected, strong fluorescence signals were observed in the tumors of the mice (n=4) into which the PB-BSA-ICG nanoparticles were injected, and signals of the major organs were extremely low (FIG. 9a). On the other hand, although the tumors of the mice into which free ICG was injected exhibited low signals, livers thereof exhibited significantly high fluorescence signals (FIG. 9b). A tendency similar to this was also observed in lungs of the free ICG-injected mice.

Such observation proves that the PB-BSA-ICG nanoparticles can be selectively accumulated in tumor tissue and can be used for diagnostic purposes by dual mode MR imaging and NIR fluorescence imaging.

Quantitative analysis of the fluorescence signals obtained from resected major tissues showed that accumulation of the PB-BSA-ICG nanoparticles in the tumors was 3.5 times higher than in livers.

Figure 10A:
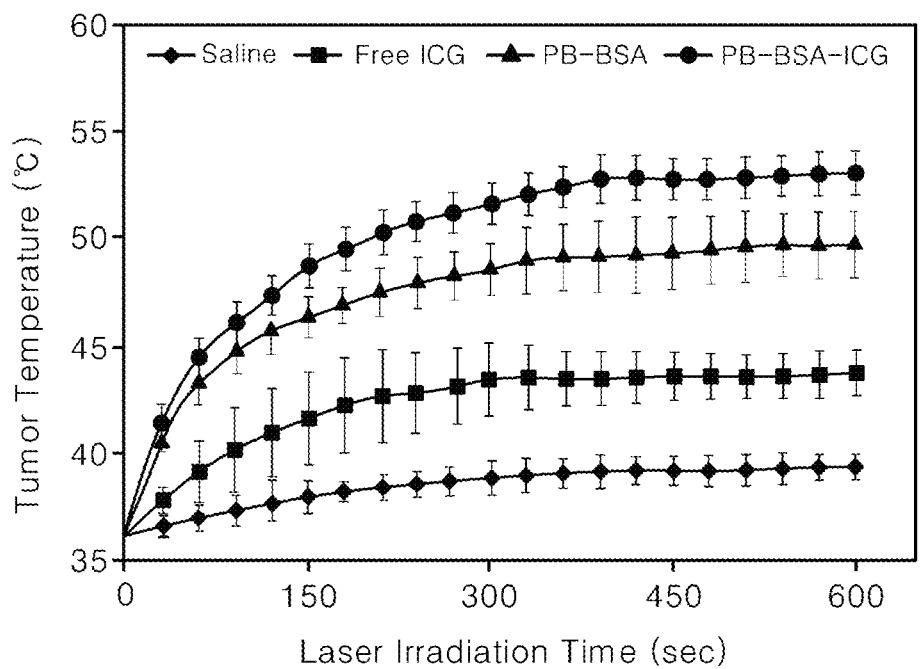
FIG. 10a is a graph depicting temperature changes of tumor sites during NIR laser irradiation.
Figure 10B:
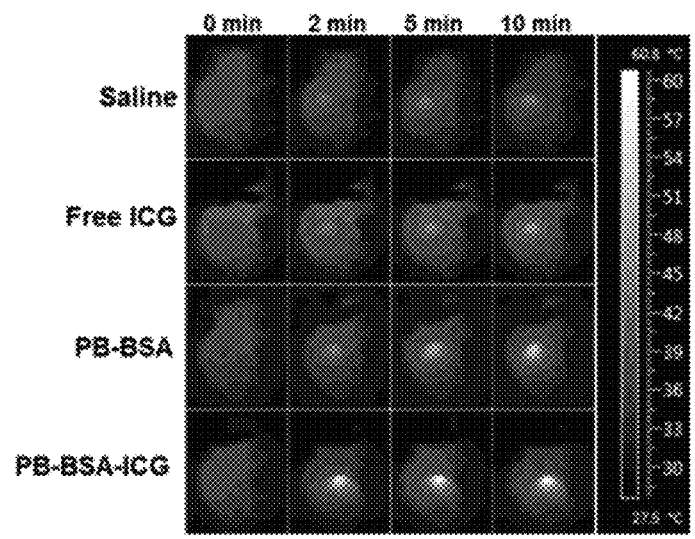
FIG. 10b shows IR thermal images of tumor-related mice during laser irradiation.
Figure 10C:
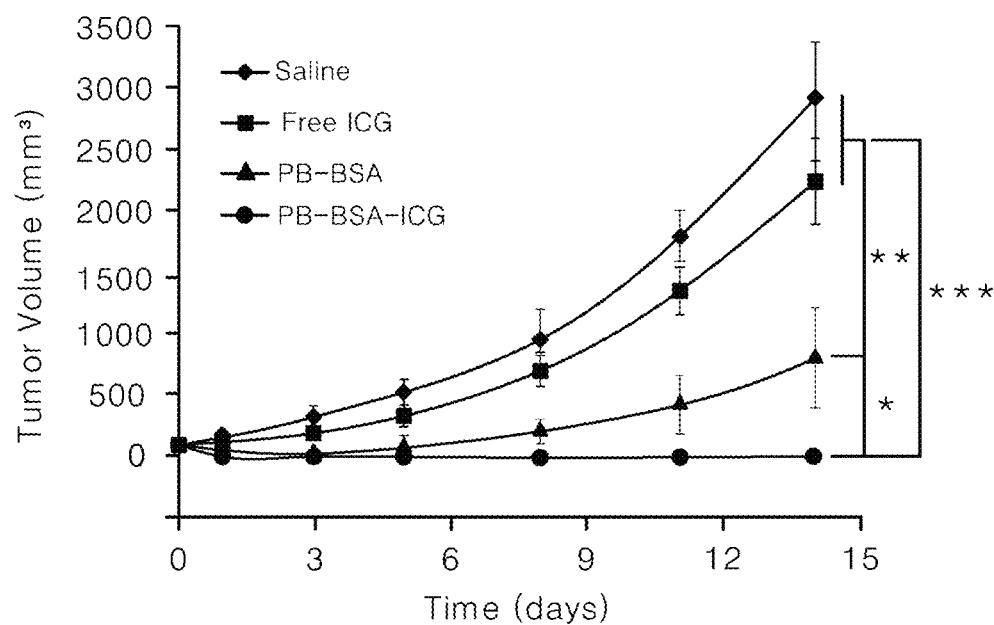
FIG. 10c is a graph depicting tumor volume changes of mice, as measured after treatment by phototherapy.
Figure 10D:
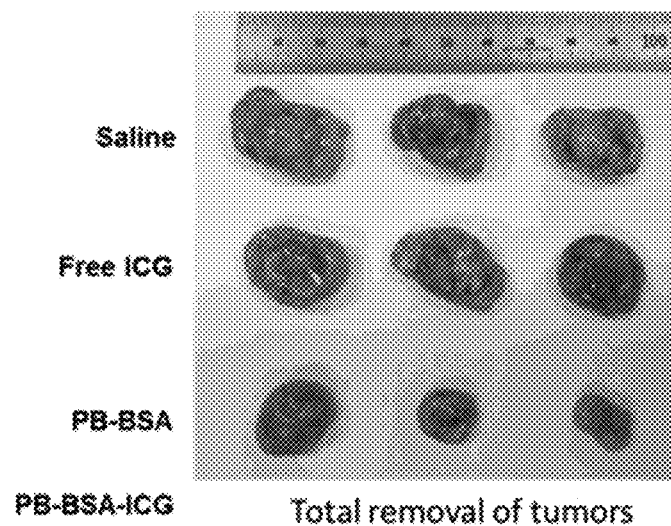
FIG. 10d is an image showing tumor tissues resected after phototherapy for 14 days.

FIGS. 10a to 10d are related to an NIR laser-induced in vivo phototherapy in tumor-xenograft mice, in which FIG. 10a is a graph depicting temperature change of tumor sites during NIR laser irradiation (808 nm, 1 W/cm$^2$); FIG. 10b shows IR thermal images of the tumor-related mice during laser irradiation; FIG. 10c is a graph depicting tumor volume changes of the mice, as measured after treatment by phototherapy ((n=3, *π<0.05, π<0.01, *π<0.001); and FIG. 10d is an image showing tumor tissues resected after phototherapy for 14 days.

Figure 11:
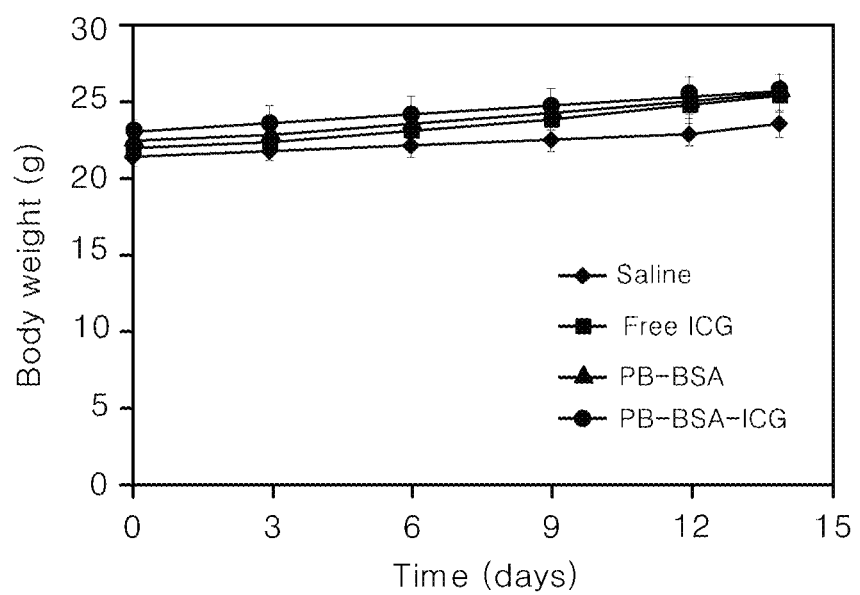
FIG. 11 is a graph depicting weight change of tumor-related mice treated by phototherapy after intravenous infusion of each of a saline solution, free ICG, PB-BSA nanoparticles, and PB-BSA-ICG nanoparticles into the mice.

In addition, FIG. 11 is a graph depicting weight change of the tumor-related mice treated by phototherapy after intravenous infusion of each of a saline solution, free ICG, the PB-BSA nanoparticles, and the PB-BSA-ICG nanoparticles into the mice.

Excellent bio-distribution and high tumor localization of the PB-BSA-ICG nanoparticles increase in vivo treatability. The tumor-containing mice were randomly divided into four groups (saline solution, free ICG, PB-BSA nanoparticles, and the PB-BSA-ICG nanoparticles), and each sample was injected through a tail vein.

24 hours after injection, tumor sites of all of the mice were irradiated with a continuous wave NIR laser beam (808 nm, 1 W/cm$^2$, 10 minutes) for phototherapy, and real-time temperature increase during laser irradiation was monitored by an IR thermal camera (FIGS. 10a and 10b).

The temperature increase was minimized in the mice subjected to injection of the saline solution, and a final temperature in the tumors was limited to 39° C. due to the absence of a photothermal agent. The mice of the free ICG group exhibited an average temperature increase of about 6° C., and a final temperature of the tumors was 42° C. Although ICG exhibits excellent photothermal conversion efficiency, photothermal instability and poor tumor localization thereof cause inefficient photothermal effects.

On the other hand, the mice subjected to injection of the PB-BSA nanoparticles exhibited a sharp increase in tumor temperature up to 49° C. due to high tumor accumulation and excellent photothermal stability, and the mice subjected to injection of the PB-BSA-ICG nanoparticles exhibited a sharp increase in tumor temperature up to 55° C. (FIGS. 10a and 10b). Targeted tumor sites had a higher temperature than surrounding regions, and the PB-BSA-ICG nanoparticles exhibited higher photothermal effects than the PB-BSA nanoparticles due to a synergistic effect of PB and ICG.

Tumor growth after laser treatment was monitored for 2 weeks and it was observed that all of the mice subjected to injection of each of the PB-BSA nanoparticles and the PB-BSA-ICG nanoparticles survived for this time period and also exhibited no weight reduction (FIG. 11).

In the mice subjected to injection of the saline solution, no treatment response was found and rapidly grown tumors were observed (FIG. 10c). Similarly, the mice treated with free ICG did not exhibit meaningful tumor regression as compared with the saline solution group.

In the PB-BSA group, although significant tumor regression was found in the initial stage, the tumors started to quickly grow after 5 days and prevention of regrowth of the tumors failed. However, in the mice subjected to injection of the laser-treated PB-BSA-ICG nanoparticles, complete removal of tumor tissue was observed and regrowth of the tumors was not found for 14 days (FIG. 10c). Better treatment efficiency of the PB-BSA-ICG nanoparticles than that of the PB-BSA nanoparticles seems to be due to the synergistic effect of PB and ICG. Although the presence of ICG improves only photothermal effects, ICG can derive photodynamic effects by generation of singlet oxygen under laser irradiation.

The nanoparticles for diagnosis or treatment of tumors according to the present invention include already proven biocompatible materials. Among the materials, Prussian blue (PB) is an MR contrast agent having excellent photothermal properties, and ICG is an NIR fluorescent dye having photothermal and photodynamic properties.

Therefore, the two materials treated in a single system are complementary to each other, noninvasive and relatively stable (radioactive isotope-free), and combination of images thereof can provide great potential for improved clinical diagnosis.

The combined photothermal-photodynamic phototherapy provides excellent tumor regression in mouse models in which the nanoparticles according to the present invention are intravenously infused.

Therefore, the multifunctional nanoparticles for diagnosis or treatment of tumors according to the present invention can provide various platforms for improved imaging and phototherapy application.

—Material and Apparatus

Materials: DMEM, fetal bovine serum (FBS), penicillin-streptomycin and trypsin-EDTA were purchased from Gibco Co., Ltd. (Grand Island, N.Y., USA); WST-8 was purchased from Dojindo Laboratories Co., Ltd. (Kumamoto, Japan); and squamous cell carcinoma (SCC7) cell lines were obtained from the Korean Cell Line Bank (Seoul, Korea).

Properties of impregnation of PB nanoparticles and ICG: The sizes and surface properties of the PB-BSA nanoparticles and the PB-BSA-ICG nanoparticles were analyzed by dynamic laser scattering (DLS) measurement, and the shapes of the nanoparticles were analyzed by AFM (NanoScope, Digital Instruments-Veeco, Santa Barbara, Calif., USA).

Stability of the PB-BSA nanoparticles was evaluated using a buffer solution (0.1 M PBS, pH 7.4) and a cell culture medium (DMEM containing 10% FBS).

The freeze-dried PB-BSA nanoparticles were re-suspended in deionized water (DIW), PBS or a medium and then subjected to shaking culture at 37° C. to be kept, and size distribution of the nanoparticles was obtained at several time points by DLS measurement.

Analysis of in vitro MR and T1 relaxation: T1-weighted MR images and T1 relaxation for different concentrations of the nanoparticles according to the present invention in deionized water were measured by a 3T clinical MRI apparatus (Magnetom Tim Trio, Siemens Medical Solutions Inc., Erlangen, Germany). Echo time was set to 12 ms; repetition time: 100 ms, 200 ms, 300 ms, 400 ms, 500 ms, 600 ms, 700 ms, 800 ms, 1000 ms, 1200 ms, 1500 ms, and 1800 ms; visual field: 24 cm; cross-sectional thickness: 3 mm; and matrix: 256×256.

Photothermal properties: Free ICG, the PB-BSA nanoparticles and the PB-BSA-ICG nanoparticles were irradiated with a 808 nm continuous wave (CW) laser beam (Dragon Lasers Co., Ltd., Changchun, China), followed by analyzing photothermal efficiency thereof. The PB concentration was 80 μm/ml and the ICG concentration was 80 μm/ml.

500 μl of each of the solutions was placed in a centrifuge tube and irradiated with an NIR laser beam at a power density of 1 W/cm$^2$ and temperature change of the solutions receiving the laser beam was measured in real time by an infrared (IR) thermal imaging system (FLIR SC-300, FLIR Systems Inc., Danderyd, Sweden).

In-vitro cell studies: The SCC7 tumor cell lines were kept in 10% FBS-containing DMEM and a 1% antibiotic solution (penicillin-streptomycin). For confirmation of in vitro toxicity, SCC7 cells were seeded in a 96-well plate ($1\times10^4$ cells/well) and cultured at 37° C. in a $CO_2$ incubator for 8 hours. Next, the nanoparticles having a concentration of 10 µg/ml to 100 µg/ml were added to the cells. 24 hours after culture, a supernatant was removed, cells were cleaned, and a fresh medium containing a WST-8 reagent was added to the wells.

The cells were further cultured at 37° C. for 1 hour, and absorbance of a color of the medium was measured at 450 nm by a multi-well spectrophotometer (SpectraMax M2e, Molecular Devices Co., Ltd., Sunnyvale, Calif., USA).

Cellular uptake of the PB-BSA-ICG nanoparticles was analyzed and quantified by flow cytometry. The SCC7 cells were treated with each of free ICG (10 µg/ml) and the PB-ICG nanoparticles (PB: 80 µg/ml, ICG: 10 µg/ml) for 24 hours. Next, the cells were cleaned 3 times with PBS separated by trypsin, and collected by centrifugation (at 1500 rpm for 5 minutes). The obtained cells were redispersed in cold PBS containing 10% FBS, and immediately analyzed by flow cytometry (FACS Calibur, BD Biosciences Co., Ltd., San Jose, Calif., USA). 30,000 events were collected for each sample, and SCC7 cells without any treatment was used as a control.

For determination of effects of laser induced phototherapy, the cells were seeded as described above, and treated with each of free ICG (10 µg/ml), the PB-BSA nanoparticles (80 µg/ml) and the PB-BSA-ICG nanoparticles (80 µg/ml) for 24 hours. Next, the cells were completely cleaned and fresh medium was added to each of the wells. Next, the cells were irradiated with an 808 nm NIR laser beam for 5 minutes.

After laser irradiation, the cells were further cultured for 12 hours, and cell viability was measured by WST-1 analysis.

In-vivo MR imaging and bio-distribution: BALB/c athymic mice (male, 6 weeks to 7 weeks) were purchased from Orient Bio Inc. (Seoul, Korea) and treated in accordance with guidelines of Animal Care and Use Committee of Gwangju Institute of Science and Technology (GIST). The SCC7 cells ($1\times10^6$ cells in 50 µl serum free DMEM media) were grafted into a right rear side region of each of the mice by subcutaneous injection.

After allowing the tumors to grow for 10 days to 12 days to a volume of about 100 $mm^3$ to about 150 $mm^3$, the PB-BSA-ICG nanoparticle solution (PB: 20 mg/kg, ICG: 2 mg/kg) was injected through a tail vein of each of the mice. T1-weighted MR imaging of the tumors was performed using a 3T clinical MRI apparatus (Magnetom Tim Trio, Siemens Medical Solutions Inc., Erlangen, Germany) before and after sample injection.

In-vivo bio-distribution of the PB-BSA-ICG nanoparticles and free ICG was analyzed by optical fluorescence imaging. After MR imaging, NIR fluorescence signals in the mice subjected to injection of the PB-BSA-ICG nanoparticles were recorded using an IVIS 100 imaging system (Xenogen Co., Ltd., Alameda, Calif., USA) after 3 hours, 6 hours, 12 hours, and 24 hours. Fluorescence signals in the mice subjected to injection of free ICG (2 mg/kg) were also recorded at time intervals similar to those set forth above.

The mice were sacrificed 24 hours after injection, and fluorescence signals (liver, lung, spleen, heart, and kidney) from resected tumors and major organs were measured.

In-vivo phototherapy: The tumor-xenograft mice were produced in the same manner as described above. The mice, in which tumors had grown to a desired volume (about 100 $mm^3$), were divided into four groups, that is, a saline solution group, a free ICG group, a PB-BSA nanoparticle group, and PB-BSA-ICG nanoparticle group. According to the groups, each sample was injected into a vein of the corresponding mouse (administration of 2 mg/kg of ICG, administration of 20 mg/kg of PB).

24 hours after injection, the tumor of each of the mice was exposed to an 808 nm NIR laser beam (1 $W/cm^2$) for 10 minutes, real-time temperature change of the tumor region during laser treatment was monitored by an IR thermal imaging system. The size of the tumor after treatment was measured at a specific time point using a digital caliper.

What is claimed is:

1. Nanoparticles for diagnosis or treatment of tumors, comprising:
    a core comprising a Prussian blue dye; and
    a shell obtained by partially or completely coating a surface of the Prussian blue core with albumin,
    wherein
    the Prussian blue dye consists of iron (III) hexacyanoferrate mixed with $Fe_4[Fe(CN)_6]_3 \cdot xH_2O$,
    the albumin of the shell is impregnated with a near-infrared fluorescent dye,
    the near-infrared fluorescent dye is bonded to the albumin in a non-covalent manner and allows a signal thereof to be sensed by a near-infrared fluorescence imaging apparatus,
    the near-infrared fluorescent dye comprises indocyanine green (ICG), and the ICG is present in an amount ranging from 1 wt % to 50 wt % in the nanoparticles,
    the nanoparticles are nontoxic in the absence of light,
    the nanoparticles generate reactive oxygen species and increase a temperature of an in vivo tumor of a mammal to 55° C. or more when irradiated with a near-infrared beam, and
    the Prussian blue dye is mixed with the albumin in a molar ratio ranging from 20:1 to 80:1.

2. The nanoparticles according to claim 1, wherein the near-infrared fluorescent dye further comprises at least one selected from the group consisting of Cy3.5, Cy5, Cy5.5, Cy7, cypate, and methylene blue.

3. The nanoparticles according to claim 1, comprising: at least one selected from the group consisting of photodynamic therapeutic drugs of porphyrin, methylene blue or phthalocyanine; and anticancer agents of paclitaxel, doxorubicin, curcumin or docetaxel.

4. The nanoparticles according to claim 1, wherein the nanoparticles increase a temperature of an in vivo tumor of mammals except humans to 45° C. or more when irradiated with a near-infrared laser beam.

5. The nanoparticles according to claim 1, wherein the nanoparticles are nontoxic in the absence of light and generate reactive oxygen species while increasing a temperature of an in vivo tumor of mammals except humans to 45° C. or more.

6. The nanoparticles according to claim 1, wherein the nanoparticles exhibit a fluorescence signal at a tumor site 2 or more times than that at a non-tumor site.

* * * * *